(12) United States Patent
Park et al.

(10) Patent No.: US 11,028,264 B2
(45) Date of Patent: Jun. 8, 2021

(54) POLYLYSINE POLYMERS WITH ANTIMICROBIAL AND/OR ANTICANCER ACTIVITY

(71) Applicants: International Business Machines Corporation, Armonk, NY (US); Agency For Science, Technology And Research, Singapore (SG)

(72) Inventors: Nathaniel H. Park, San Jose, CA (US); James L. Hedrick, Pleasanton, CA (US); Victoria A. Piunova, Los Gatos, CA (US); Gavin Jones, San Jose, CA (US); Yi Yan Yang, Singapore (SG); Pang Kern Jeremy Tan, Singapore (SG); Chuan Yang, Hillington Green (SG); Cherylette Anne Alexander, Singapore (SG)

(73) Assignees: INTERNATIONAL BUSINESS MACHINES CORPORATION, Armonk, NY (US); AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 16/531,432

(22) Filed: Aug. 5, 2019

(65) Prior Publication Data

US 2021/0040319 A1 Feb. 11, 2021

(51) Int. Cl.
*A61K 45/06* (2006.01)
*C08L 79/02* (2006.01)

(52) U.S. Cl.
CPC .............. *C08L 79/02* (2013.01); *A61K 45/06* (2013.01)

(58) Field of Classification Search
None
See application file for complete search history.

(56) References Cited

U.S. PATENT DOCUMENTS

| 9,854,806 | B2 | 1/2018 | Chin et al. |
| 9,976,074 | B2 | 5/2018 | Stanciu et al. |
| 2011/0311463 | A1* | 12/2011 | Diamond ............... A61K 8/046 424/47 |
| 2012/0045400 | A1* | 2/2012 | Nowak .................. A61Q 11/00 424/48 |

(Continued)

FOREIGN PATENT DOCUMENTS

| CN | 108694991 A | 10/2018 | |
| FR | 2851465 A1 * | 8/2004 | ............... A61Q 5/12 |

(Continued)

OTHER PUBLICATIONS

List of IBM Patents or Applications Treated as Related.

(Continued)

*Primary Examiner* — Brian Gulledge
(74) *Attorney, Agent, or Firm* — Amin, Turocy & Watson, LLP

(57) ABSTRACT

Techniques regarding guanidinium functionalized polylysine polymers that can have antimicrobial and/or anticancer activity are provided. For example, one or more embodiments described herein can comprise a chemical composition, which can comprise a polymer comprising a molecular backbone covalently bonded to a pendent guanidinium functional group, wherein the molecular backbone can comprise a polylysine structure.

20 Claims, 16 Drawing Sheets

(56) References Cited

U.S. PATENT DOCUMENTS

| | | |
|---|---|---|
| 2014/0193517 A1 | 7/2014 | Agarwal et al. |
| 2015/0038671 A1 | 2/2015 | Parang et al. |
| 2016/0338356 A1 | 11/2016 | Chen et al. |
| 2018/0020669 A1 | 1/2018 | Charles et al. |
| 2018/0157786 A1 | 6/2018 | Dakshanamurthy et al. |
| 2019/0388460 A1 | 12/2019 | Hedrick et al. |

FOREIGN PATENT DOCUMENTS

| | | |
|---|---|---|
| WO | 2005/007098 A2 | 1/2005 |
| WO | 2016024999 A1 | 2/2016 |
| WO | 2016123368 A1 | 8/2016 |
| WO | 2016/0186581 A1 | 11/2016 |
| WO | 2017053778 A1 | 3/2017 |
| WO | 2017066242 A1 | 4/2017 |
| WO | 2018015665 A1 | 1/2018 |

OTHER PUBLICATIONS

Kolpin, Dana W., et al. "Pharmaceuticals, Hormones and Other Organic Wastewater Contaminants in U.S. Streams, 1999-2000: A National Reconnaissance." Environ. Sci. and Technol. 2002, 36, 1202-1211. 12 pages.

Hoque, Jiaul, et al. "Broad Spectrum Antibacterial and Antifungal Polymeric Paint Materials: Synthesis, Structure-Activity Relationship, and Membrane-Active Mode of Action." ACS Appl. Mater. Interfaces 2015, 7, 1804-1815. DOI: 10.1021/am507482y. 12 pages.

Harbut et al. "Auranofin exerts broad-spectrum bactericidal activities by targeting thiol-redox homeostasis." Proceedings of the National Academy of Sciences. (2015). 6 pages.

Padhy et al. "Drug repositioning: Re-investigating existing drugs for new therapeutic indications." Journal Postgraduate Medicine 57(2), p. 153. (2011). 10 pages.

Younis et al. "Repurposing nonantimicrobial drugs and clinical molecules to treat bacterial infections." Current Pharmaceutical Design, 21(28), pp. 4106-4111. (2015). 11 pages.

Brochado et al. "Species-specific activity of antibacterial drug combinations" Nature International Journal of Science Jul. 4, 2018. 42 pages.

Chin et al., "A macromolecular approach to eradicate multidrug resistant bacterial infections while mitigating drug resistance onset", Nature Communications Article DOI: 10.1038/s41467-018-03325-6 (2018). 14 pages.

Piccaro et al., "Rifampin Induces Hydroxyl Radical Formation in *Mycobacterium tuberculosis*", AAC Journals.ASM.org Antimicrobial Agents and Chemotherapy p. 7527-7533 vol. 58 No. 12 Dec. 2014. 7 pages.

Hedrick, et al. "Utilizing Polymers and Antibiotics to Enhance Antimicrobial Activity and Inhibit Antibiotic Resistance" U.S. Appl. No. 16/144,040, filed Sep. 27, 2018. 56 pages.

Non-Final Office Action received for U.S. Appl. No. 16/531,493 dated Jul. 23, 2020, 66 pages.

Cho et al., "Molecular Weight and Charge Density Effects of Guanidinylated Biodegradable Polycarbonates on Antimicrobial Activity and Selectivity", Biomacromolecules, 2017, vol. 19, pp. 1389-1401.

Ogrendik et al., "Antibiotics for the treatment of rheumatoid arthritis", International Journal of General Medicine, 2013, vol. 7, pp. 43-47.

Dall et al., "Synthetic polymers show promise against multidrugresistant microbes", University of Minnesota (CIDRAP, Synthetic polymers show promise against-multidrug resistance, Apr. 9, 2018, 3 pages.

Thangamani et al., "Antibacterial activity and mechanism of action of auranofin against multi-drug resistant bacterial pathogens", Scientific Reports, 2016, vol. 6, pp. 1-13.

International Search Report and Written Opinion received for PCT Application Serial Appl. No. PCT/162020/056650 dated November 3, 2020, 11 pages.

El-Sersy et al., "Antibacterial and Anticancer activity of ε-poly-L-lysine (ε-PL) produced by a marine Bacillus subtilis sp. ", Journal of Basic Microbiology., vol. 52, Dec. 31, 2012, 10 pages.

Santos et al., "Recent Developments in Antimicrobial Polymers: A Review", Materials, vol. 9, Jul. 20, 2016, 33 pages.

Pantos et al., "Guanidinium group: A versatile moiety inducing transport and multicompartmentalization in complementary membranes", Biochimica et Biophysica Acta vol. 1778, Dec. 12, 2008, pp. 811-823.

Exley et al., "Antimicrobial Peptide Mimicking Primary Amine and Guanidine Containing Methacrylamide Copolymers Prepared by Raft Polymerization", Biomacromolecules., vol. 16 Nov. 11, 2015, pp. 3845-3852.

International Search Report and Written Opinion received for PCT Application Serial No. PCT/IB2020/056644 dated Nov. 3, 2020, 11 pages.

Song et al., "β-methasone-containing biodegradable poly(lactide-coglycolide) acid microspheres for intraarticular injection: effect of formulation parameters on characteristics and in vitro release", Pharmaceutical Development and Technology, vol. 18, No. 5, Dec. 31, 2013, pp. 1220-1229.

Pearson et al., "Glycopolymer Self-Assemblies with Gold(I)Complexed to the Core as a Delivery System for Auranofin", Macromolecules, vol. 48, Jan. 23, 2015, pp. 118-125.

Dangol et al., "Innovative polymeric system (IPS) for solvent-free lipophilic drug transdermal delivery via dissolving microneedle", Journal of Controlled Release, vol. 223, Dec. 28, 2015, 25 pages.

\* cited by examiner

Table 2

| Chemical Compound | S. aureus (μg/mL) | E. coli (μg/mL) | P. aeruginosa (μg/mL) | C. albicans (μg/mL) |
|---|---|---|---|---|
| non-functionalized polylysine | 7.8 | 7.8 | 3.9 | 15.6 |
| first chemical structure 100 (~50% guanidination) | 31.3 | 15.6 | 15.6 | 125 |
| first chemical structure 100 (~70% guanidination) | 15.6 | 15.6 | 15.6 | 125 |
| first chemical structure 100 (~90% guanidination) | 15.6 | 15.6 | 7.8 | 125 |
| first chemical structure 100 (~100% guanidination) | 15.6 | 15.6 | 1.8 | 62.5 |
| first chemical structure 100 (~50% guanidination) + fourth chemical structure 606 (~100% sulfonation) | >500 | >500 | >500 | >500 |
| first chemical structure 100 (~70% guanidination) + fourth chemical structure 606 (~100% sulfonation) | 250 | Increasing level of precipitation | | |
| first chemical structure 100 (~90% guanidination) + fourth chemical structure 606 (~100% sulfonation) | >500 | | | |

FIG. 8A

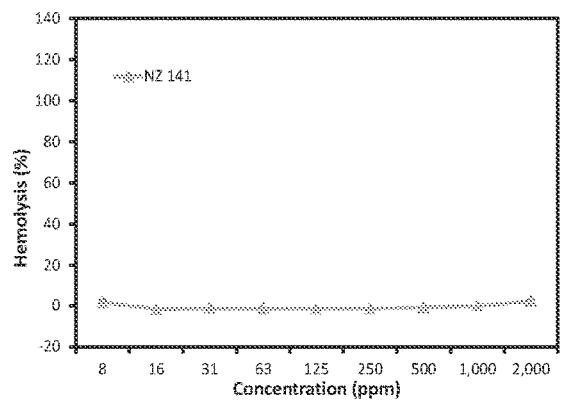

FIG. 8B

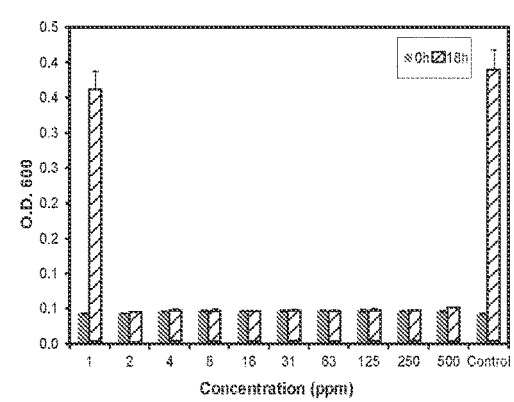

FIG. 8C

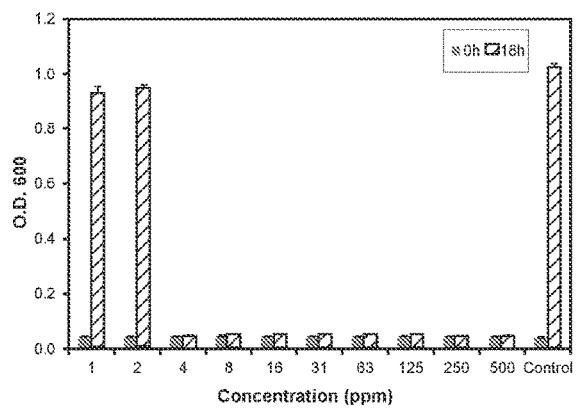

FIG. 8D

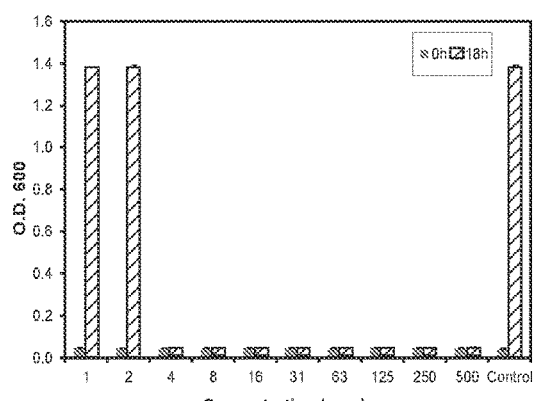

FIG. 8E

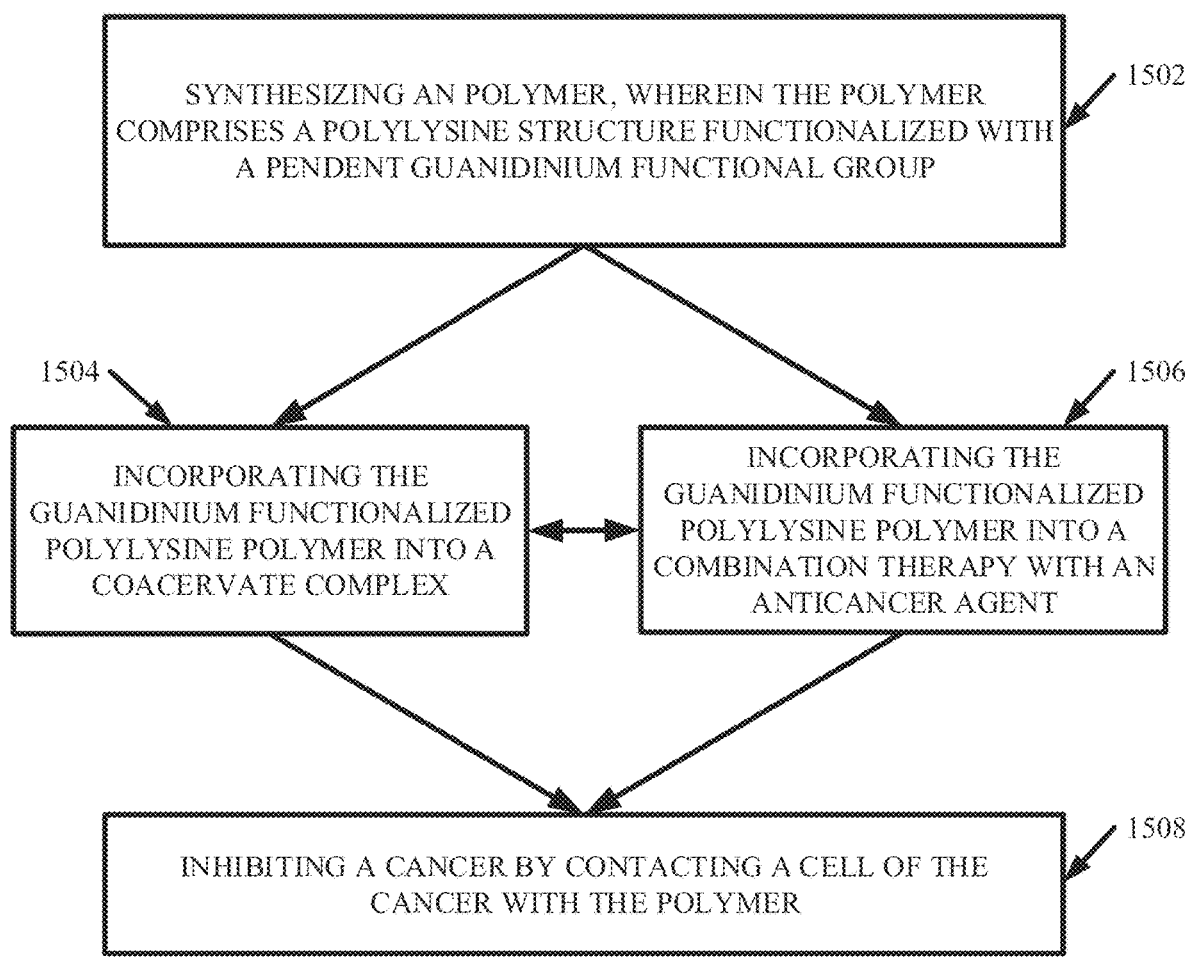

POLYLYSINE POLYMERS WITH ANTIMICROBIAL AND/OR ANTICANCER ACTIVITY

BACKGROUND

The subject disclosure relates to antimicrobial and/or anticancer polymers, and more specifically, to one or more polylysine polymers that can exhibit antimicrobial activity and/or anticancer activity along with compatibility with complex formulations (e.g., anionic surfactants).

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, chemical compounds and/or methods regard polylysine polymers functionalized with one or more guanidinium groups are described.

According to an embodiment, a chemical composition is provided. The chemical composition can comprise a polymer comprising a molecular backbone covalently bonded to a pendent guanidinium functional group, wherein the molecular backbone comprises a polylysine structure.

According to an embodiment, a method is provided. The method can comprise inhibiting a pathogen by contacting a cell of the pathogen with an antimicrobial polymer. The antimicrobial polymer can comprise a polylysine structure functionalized with a pendent guanidinium functional group.

According to an embodiment, a method is provided. The method can comprise inhibiting a cancer by contacting a cell of the cancer with a polymer. The polymer can comprise a polylysine structure functionalized with a pendent guanidinium functional group.

BRIEF DESCRIPTION OF THE DRAWINGS

FIG. 8A illustrates a diagram of an example, non-limiting table that can depict the antimicrobial activity of one or more polymers and/or coacervate complexes in accordance with one or more embodiments described herein.

FIG. 8B illustrates a diagram of an example, non-limiting graph that can depict the hemolytic activity of one or more guanidinium-functionalized polylysine polymers in accordance with one or more embodiments described herein.

FIG. 8C illustrates a diagram of an example, non-limiting graph that can depict the hemolytic activity of one or more guanidinium-functionalized polylysine polymers in accordance with one or more embodiments described herein.

FIG. 8D illustrates a diagram of an example, non-limiting graph that can depict the hemolytic activity of one or more guanidinium-functionalized polylysine polymers in accordance with one or more embodiments described herein.

FIG. 8E illustrates a diagram of an example, non-limiting graph that can depict the hemolytic activity of one or more guanidinium-functionalized polylysine polymers in accordance with one or more embodiments described herein.

FIG. 15 illustrates a flow diagram of an example, non-limiting method that can inhibiting one or more cancers using one or more guanidinium-functionalized polylysine polymers with antimicrobial and/or anticancer activity in accordance with one or more embodiments described herein.

DETAILED DESCRIPTION

Figure 1:
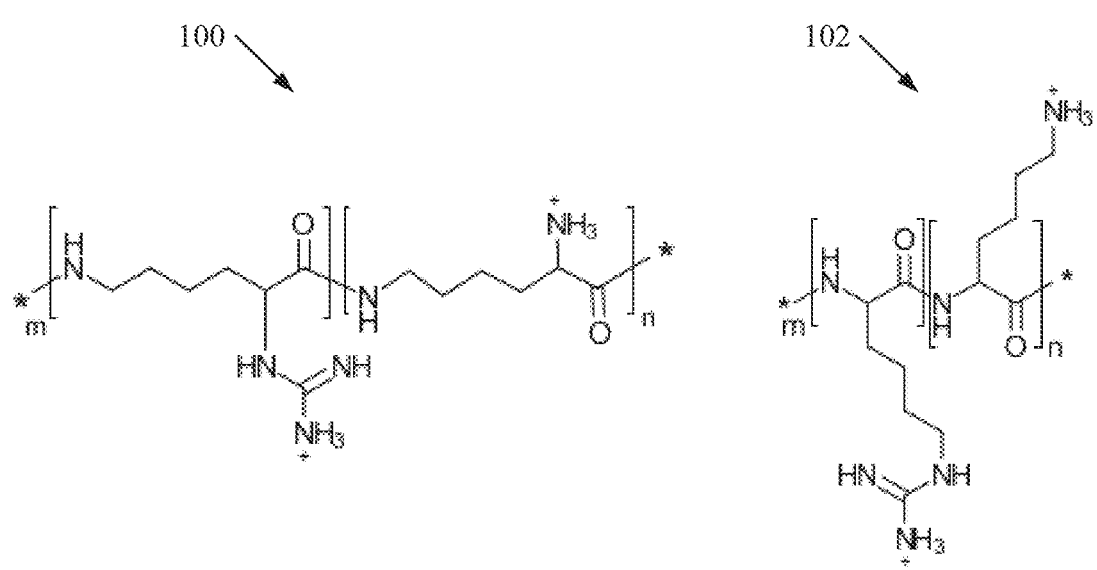
FIG. 1 illustrates a diagram of example, non-limiting chemical structures that can characterize one or more guanidinium-functionalized polylysine polymers having antimicrobial and/or anticancer activity in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Antimicrobial agents are pervasively used in consumer products to prevent infections and to prolong product shelf-life. Most antimicrobial agents found in consumer goods have molecular weights below 500 daltons (Da) and include anilides (e.g. triclocarban), bis-phenols (e.g. triclosan), biguanides (e.g. chlorhexidine) and/or quaternary ammonium compounds (e.g. cetylpyridium chloride and cetrimide). Triclosan is one of the most commonly used compounds and is found in more than 50% of consumer products including soap, deodorant, toothpaste, mouth wash and cosmetics. It is effective against Gram-positive bacteria, while having little activity against Gram-negative bacteria and molds. Most of the antimicrobial agents listed above manifest resistance to many strains of bacterial spores (e.g. *Clostridium* species), Gram-positive (e.g. mycobacteria) and Gram-negative bacteria (e.g., *Pseudomonas aeruginosa*). More importantly, a major concern is the development of cross- and co-resistance with clinically used antibiotics, further complicating the resistance dilemma. Despite efforts to exploit newly discovered biochemical pathways and cellular targets within microbes, the chemical compound development pipeline for new antibiotics has not been able to keep pace with the rate of development new antibiotic-resistant bacterial strains discovered year after year.

Various embodiments described herein can regard chemical compositions comprising one or more polylysine polymers functionalized with one or more pendent guanidinium functional groups. Additionally, the one or more guanidinium functionalized polylysine polymers can exhibit antimicrobial and/or anticancer activity. For example, one or more embodiments can regard inhibiting a pathogen (e.g., one or more bacteria infections) by contacting one or more cells of the pathogen with the one or more guanidinium functionalized polylysine polymers. Also, one or more embodiments can regard inhibiting a cancer by contacting one or more cells of the cancer with the one or more guanidinium functionalized polylysine polymers. In various embodiments, the one or more guanidinium functionalized polylysine polymers can have varying amounts of functionalization by the one or more pendent guanidinium functional groups. Further, the one or more guanidinium functionalized polylysine polymers can be compatible with a variety of complex formulations, such as anionic surfactants.

As depicted in FIGS. 1-5, "m" can represent a number that is, for example, greater than or equal to 5 and less than or equal to 30, and/or "n" can represent a number that is, for example, greater than or equal to 0 and less than or equal to 25. Additionally, the "*" can represent: one or more repetitions of all and/or parts of the structures shown, one or more hydrogens, an alkyl group, an aryl group, a combination thereof, and/or the like. Unless otherwise stated, materials utilized to facilitate the experiments, tables, charts, diagrams, and/or the like described herein can be acquired from the following sources. The bacteria *Staphylococcus aureus* ("*S. aureus*", ATCC 29737), *Escherichia coli* ("*E. coli*", ATCC 25922), *Pseudomonas aeruginosa* ("*P. aeruginosa*", ATCC 9027), *Candida albicans* ("*C. albicans*", ATCC 10231), and/or *Klebsiella pneumoniae* ("*K. pneumoniae*", ATCC700603) were acquired from American Type Culture Collection ("ATCC").

FIG. 1 illustrates a diagram of an example, non-limiting first chemical structure 100 and/or second chemical structure 102 that can characterize one or more guanidinium functionalized polylysine polymers in accordance with one or more embodiments described herein. Repetitive description of like elements employed in other embodiments described herein is omitted for sake of brevity. As shown in FIG. 1, the one or more guanidinium functionalized polylysine polymers can comprise: α-poly-L-lysine structures (e.g., in accordance with second chemical structure 102), α-poly-D-lysine structures (e.g., in accordance with second chemical structure 102), ε-poly-L-lysine structures (e.g., in accordance with first chemical structure 100), and/or ε-poly-D-lysine structures (e.g., in accordance with first chemical structure 100).

In various embodiments, the one or more guanidinium functionalized polylysine polymers can be cationic. For example, one or more positive charges can be distributed throughout the one or more guanidinium functionalized polylysine polymers. For instance, the one or more polylysine structures can comprise one or more protonated primary amines, and/or the one or more pendent guanidinium functional groups can comprise one or more protonated amines (e.g., protonated primary amines and/or protonated secondary amines). Thereby, the one or more guanidinium functionalized polylysine polymers can disperse one or more positive charges throughout the subject polymers such that the polymers can become active in the presence of soaps and/or detergents.

In one or more embodiments, the one or more guanidinium functionalized polylysine polymers characterized by the first chemical structure 100 and/or the second chemical structure 102 can have a number-average molecular weight ("Me") ranging, for example, greater than or equal to 2,000 Da and less than or equal to 4,000 Da (e.g., 4,000 Da). Additionally, in one or more embodiments the first chemical structure 100 and/or the second chemical structure 102 can further comprise a sugar moiety covalently bonded to the molecular backbone. For example, the sugar moiety can comprise 10 mole percent or less of the one or more guanidinium functionalized polylysine polymers characterized by the first chemical structure 100 and/or the second chemical structure 102.

Figure 2:
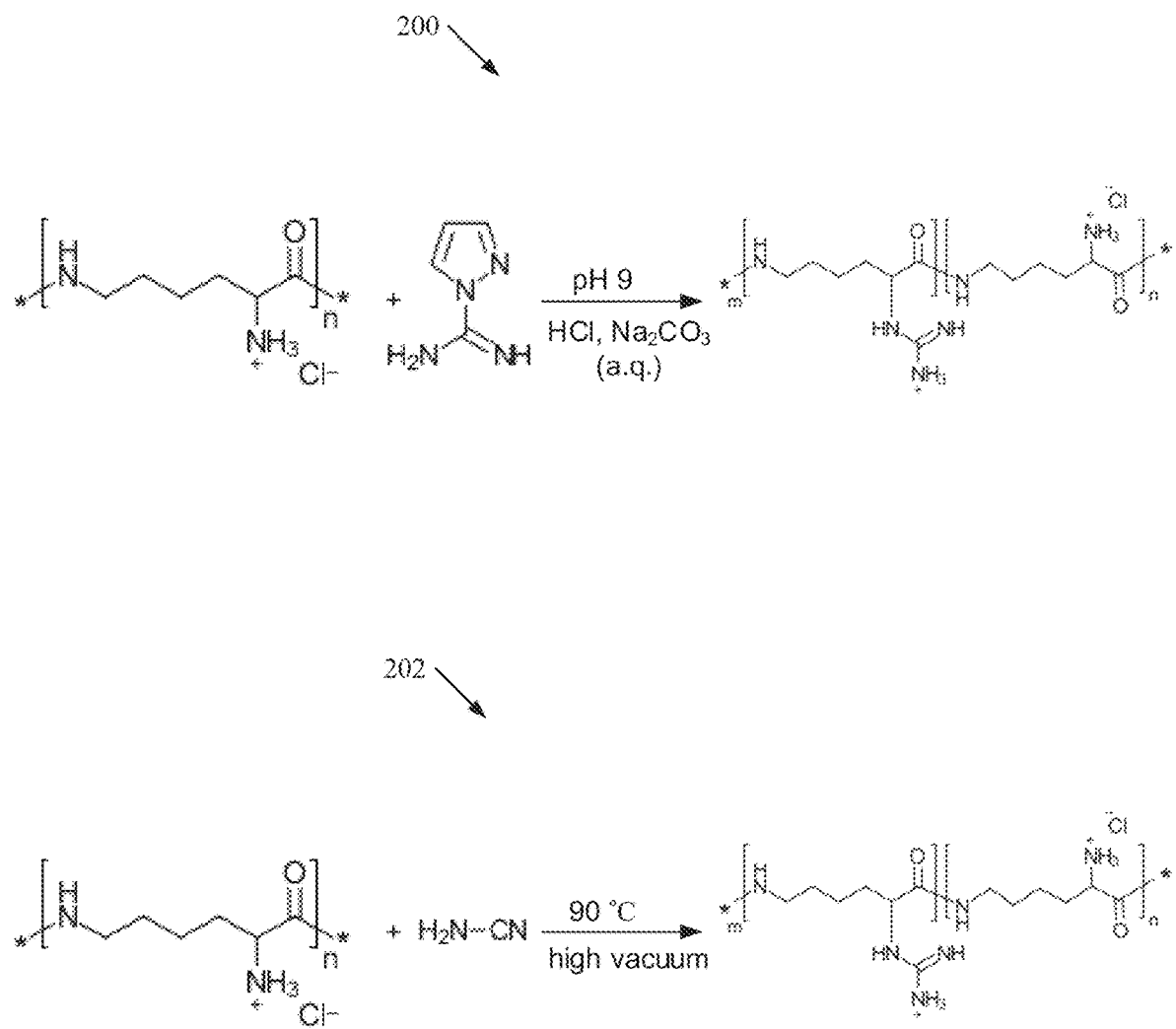
FIG. 2 illustrates a diagram of example, non-limiting polymerization schemes that can characterize synthesis of one or more guanidinium-functionalized polylysine polymers having antimicrobial and/or anticancer activity in accordance with one or more embodiments described herein.

FIG. 2 illustrates a diagram of example, non-limiting polymerization schemes that can facilitate synthesis of the one or more guanidinium functionalized polylysine polymers in accordance with one or more embodiments described herein. Repetitive description of like elements employed in other embodiments described herein is omitted for sake of brevity. The first polymerization scheme 200 depicts an exemplary synthesis of the one or more guanidinium functionalized polylysine polymers in a high potential hydron ("pH") environment. The second polymerization scheme 202 depicts an exemplary synthesis of the one or more guanidinium functionalized polylysine polymers in a high vacuum environment.

As shown in FIG. 2, the first polymerization scheme 200 can comprise reacting one or more polylysine polymers (e.g., comprising one or more ε-poly-L-lysine and/or ε-poly-D-lysine structures) with one or more guanidinium functionalized reagents. The one or more guanidinium functionalized reagents can comprise one or more guanidium functional groups. Example guanidinium functionalized reactants can include, but are not limited to, praxadine (e.g., as shown in FIG. 2) and/or the like. In various embodiments, the one or more polylysine polymers and/or guanidinium functionalized reagents can be sonicated and/or gently heated until both reagents are fully dissolved. Additionally, the one or more polylysine polymers and/or guanidinium functionalized reagents can be mixed in the presence of: sodium carbonate ("$Na_2CO_3$"), potassium carbonate, potassium phosphate tribasic, sodium phosphate, cesium carbonate, sodium hydroxide, potassium hydroxide, a combination thereof, and/or the like. Further, the one or more polylysine polymers and/or guanidinium functionalized reagents can be mixed in a high pH environment. For example, the mixing environment can have a pH that is greater than or equal to 7 and less than or equal to 14 (e.g., a pH of 9). One of ordinary skill in the art will readily appreciate that although FIG. 2 illustrates the first polymerization scheme 200 with regards to ε-polylysine structures, the architecture of the first polymerization scheme 200 is not so limited. For example, the various features of the first polymerization scheme 200 described herein can be performed with regards to one or more polylysine polymers characterized by one or more α-polylysine structures.

For example, a 20 mL scintillation vial can be charged with polylysine and dissolved in 2 molar (M) aqueous $Na_2CO_3$. Once dissolved, praxadine can be added in portions over a 16-hour period while monitoring the reaction via NMR spectroscopy. When the desired level of functionalization is attained, the reaction mixture can be precipitated into acetone. The resultant solid can be washed with additional acetone and tetrahydrofuran. The solid can then be dissolved in water and acidified (e.g., to pH~1) with concentrated HCl and then dialyzed against water (e.g., 1000 Da MWCO membrane) for 24 h, changing the water three times. Following dialysis, the sample can be lyophilized to afford the desired guanidinium functionalized polymer.

As shown in FIG. 2, the second polymerization scheme 202 can comprise reacting one or more polylysine polymers (e.g., comprising one or more ε-poly-L-lysine and/or ε-poly-D-lysine structures) with one or more cyanamide reagents. The one or more polylysine polymers and/or cyanamide reagents can be heated to a temperature ranging, for example, greater than or equal to 80 degrees Celsius (° C.) and less than or equal to 120° C. (e.g., 90° C.). Additionally, the one or more polylysine polymers and/or cyanamide reagents can be mixed in a high vacuum environment. One of ordinary skill in the art will readily appreciate that although FIG. 2 illustrates the second polymerization scheme 202 with regards to ε-polylysine structures, the architecture of the second polymerization scheme 202 is not so limited. For example, the various features of the second polymerization scheme 202 described herein can be performed with regards to one or more polylysine polymers characterized by one or more α-polylysine structures.

In various embodiments, the reagents of the first polymerization scheme 200 and/or the second polymerization scheme 202 (e.g., guanidinium functionalized reagents and/or cyanamide reagents) can be titrated over time to achieve a desired level of functionalization of the one or more polylysine polymers. As a result of the first polymerization scheme 200 and/or the second polymerization scheme 202, the one or more polylysine polymers can be functionalized with pendent guanidinium functional groups at one or more locations of the primary amines of the polylysine structures. Additionally, one or more of the primary amines not functionalized by a guanidinium group can be protonated (e.g., by the HCl). Thereby, one or more positive charges can be distributed along the molecular backbone of the one or more synthesized guanidinium functionalized polylysine polymers.

Figure 3:
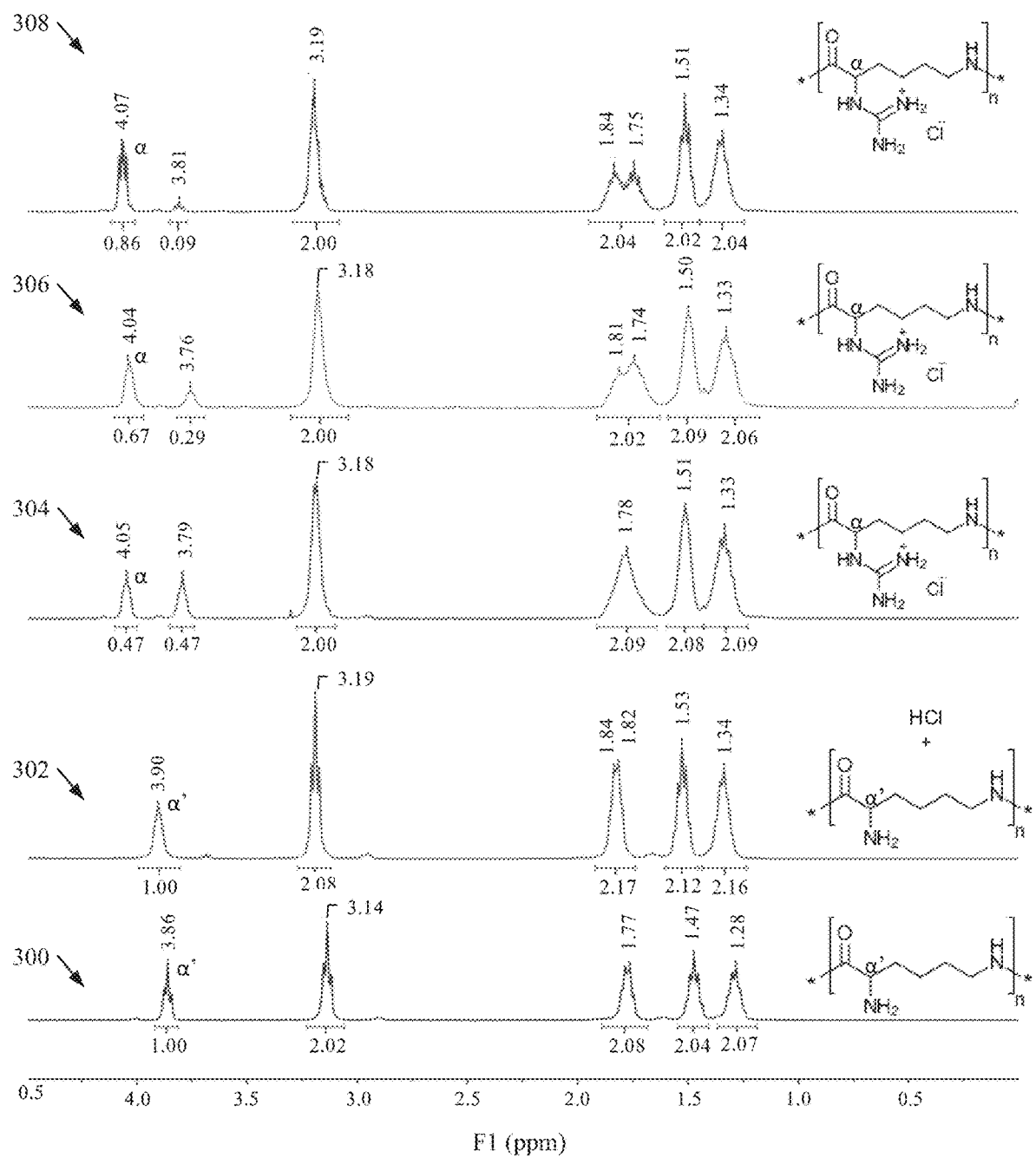
FIG. 3 illustrates a diagram of example, non-limiting graphs and corresponding nuclear magnetic resonance spectra that can depict various degrees of guanidinium functionalization of polylysine that can have antimicrobial and/or anticancer activity in accordance with one or more embodiments described herein.

FIG. 3 illustrates a diagram of example, non-limiting nuclear magnetic resonance ("NMR") graphs that can demonstrate various amounts of functionalization of the one or more guanidinium functionalized polylysine polymers in accordance with one or more embodiments described herein. Repetitive description of like elements employed in other embodiments described herein is omitted for sake of brevity. In various embodiments, the amount of functionalization of the polylysine polymers with the guanidinium groups can be monitored using NMR. As shown in FIG. 3, the alpha carbon comprised within the polylysine structures and/or bonded to a primary amine functional group can be represented by "α"; whereas alpha carbons bonded to a guanidinium functional group can be represented by "α'". By monitoring the proton shift and/or the amplitude of the peaks associated with the a and/or a' carbons, the amount of functionalization of the polylysine polymers with the guanidinium groups can be determined.

The first NMR graph 300 can correspond to a polylysine polymer in the presence of hydrogen chloride. The second NMR graph 302 can correspond to a polylysine polymer. The third NMR graph 304 can correspond to a guanidinium functionalized polylysine polymer having 50% functionalization with the one or more guanidine groups. The fourth NMR graph 306 can correspond to a guanidinium functionalized polylysine polymer having 70% functionalization with the one or more guanidine groups. The fifth NMR graph 308 can correspond to a guanidinium functionalized polylysine polymer having 90% functionalization with the one or more guanidine groups. As shown in FIG. 3, changes within the NMR graphs can correlate to changes in the amount of guanidinium functionalization experienced by the polylysine polymers.

In various embodiments, the one or more guanidinium functionalized polylysine polymers can exhibit antimicrobial activity and/or anticancer activity via one or more translocation mechanisms, which can be directed towards one or more pathogen (e.g., a Gram-negative microbe, a Gram-positive microbe, a fungi, and yeast) and/or cancer cells. At a first stage of the translocation mechanism, one or more guanidinium functionalized polylysine polymers (e.g., characterized by the first chemical structure 100 and/or the second chemical structure 102) can be attracted to a membrane of a target cell (e.g., a bacterium and/or cancer cell). In one or more embodiments, the one or more guanidinium functionalized polylysine polymers can be electrostatically attracted towards the cell membrane. For example, one or more guanidinium groups of the guanidinium functionalized polylysine polymers can be cationic and/or can be electrostatically attracted to one or more negative charges associated with the cell membrane.

At a second stage of the translocation mechanism, the one or more guanidinium functionalized polylysine polymers can pass through the cell membrane of the subject cell and enter an interior of the cell. For instance, the cell membrane (e.g., comprising a lipid bilayer) can separate the interior of the subject cell from the environment surrounding the subject cell. In various embodiments, the one or more guanidinium functional groups of the one or more guanidinium functionalized polylysine polymers can form one or more multidentate hydrogen-bonds with one or more phosphate groups in the cell membrane. The one or more multidentate hydrogen-bonds can neutralize a charge of the cell membrane, and thus can promote cell membrane translocation. Upon entering the cell, the one or more guanidinium functionalized polylysine polymers can associate with an inner leaflet of the cell membrane.

At a third stage of the translocation mechanism, the one or more guanidinium functionalized polylysine polymers can be released from the inner leaflet and can be dispersed within a cytoplasm of the cell. At a fourth stage of the translocation mechanism, the one or more guanidinium functionalized polylysine polymers can precipitate one or more cytosolic members, such as: proteins, enzymes, and/or genes (e.g., located in one or more DNA segments of the cell). For instance, the one or more guanidinium functionalized polylysine polymers can interact with one or more cytosolic proteins, enzymes, and/or genes of the cell and/or precipitate the cytosolic members. In one or more embodiments, the described interaction and/or precipitation between the one or more guanidinium functionalized polylysine polymers and the cytosolic members can result in cell apoptosis.

In various embodiments, the one or more guanidinium functionalized polylysine polymers can be comprised within one or more combination therapies to enhance the antimicrobial and/or anticancer activity of other therapeutic agents. As used herein, the term "combination therapy" can refer to the use of multiple chemical compounds to treat an illness, disease, and/or cancer. The chemical compounds can comprise pharmaceutical compounds, such as anticancer agents and/or antibiotics. Additionally, the chemical compounds can comprise compounds other than pharmaceutical compounds, such as antimicrobial polymers (e.g., functionalized polylysine polymers). The multiple chemical compounds can be used in combination to achieve one or more synergistic effects, which can enhance and/or facilitate one or more therapeutic treatments of the chemical compounds. In addition, the combination can comprise various types of chemical compounds. For example, one or more pharmaceutical compounds can be combined with one or more antimicrobial polymers in one or more combination therapies. Further, inhibiting the illness (e.g., pathogen and/or cancer) can comprise: treating the illness, eradicating the illness, delaying the illness, mitigating the illness, reducing the development of a resistance to treatment by the illness, a combination thereof, and/or the like. Moreover, the illness (e.g., an infection) can be caused by one or more microbes (e.g., bacteria, such as Gram-negative bacteria).

In one or more embodiments, the one or more guanidinium functionalized polylysine polymers can be used in a combination therapy with one or more other antimicrobial agents (e.g., antibacterial agents) to enhance the antimicrobial activity of the one or more other antimicrobial agents. Similarly, in some embodiments the one or more guanidinium functionalized polylysine polymers can be used in a combination therapy with one or more other anticancer agents to enhance the anticancer activity of the one or more other anticancer agents. Example antimicrobial agents that can be comprised within a combination therapy with the one or more guanidinium functionalized polylysine polymers can include, but are not limited to: rifampicin, imipenem, meropenem, penicillin, rifamycin, amoxicillin, ceftiofur, enrofloxacin, chlortetracycline, fluconazole, a combination thereof, and/or the like. Example anticancer agents that can be comprised within a combination therapy with the one or more guanidinium functionalized polylysine polymers can include, but are not limited to: doxorubicin, paclitaxol, 5-FU, cisplatin, gemcitabine, a combination thereof, and/or the like.

For instance, the one or more cytosolic members (e.g., proteins, enzymes, and/or genes) targeted by the one or more guanidinium functionalized polylysine polymers can inhibit the function of the one or more other antimicrobial and/or anticancer agents. Thereby, the one or more guanidinium functionalized polylysine polymers, which can be characterized by the first chemical structure 100 and/or the second chemical structure 102, can enhance the antimicrobial and/or anticancer activity of the other agents comprised within a subject combination therapy by binding and/or precipitating one or more cytosolic proteins, enzymes, and/or genes of the target cell.

Figure 4A:
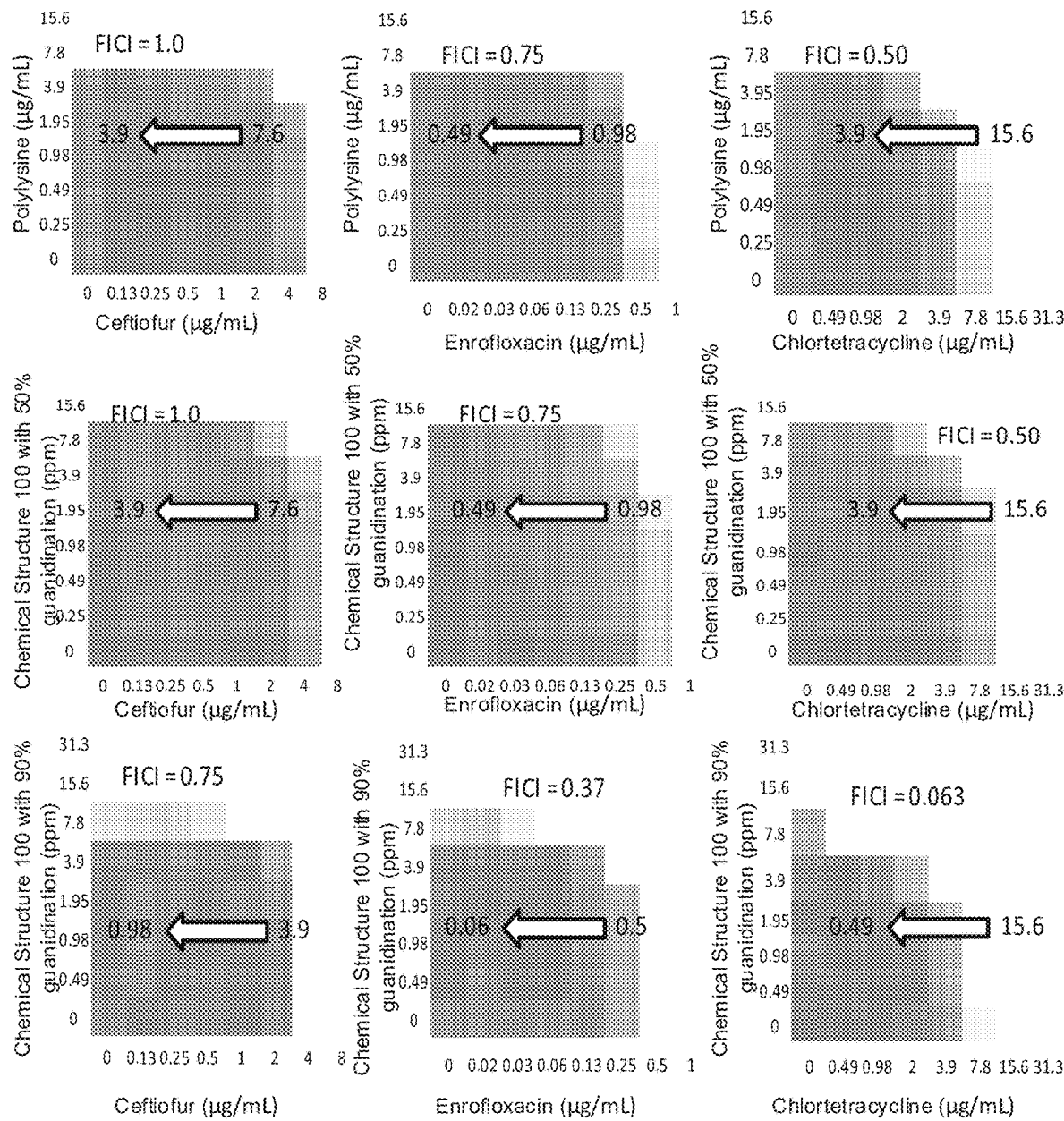
FIG. 4A illustrates a diagram of example, non-limiting graphs that can depict the efficacy of one or more combination therapies comprising one or more guanidinium functionalized polylysine polymers in combination with one or more antibiotics in accordance with one or more embodiments described herein.
Figure 4B:
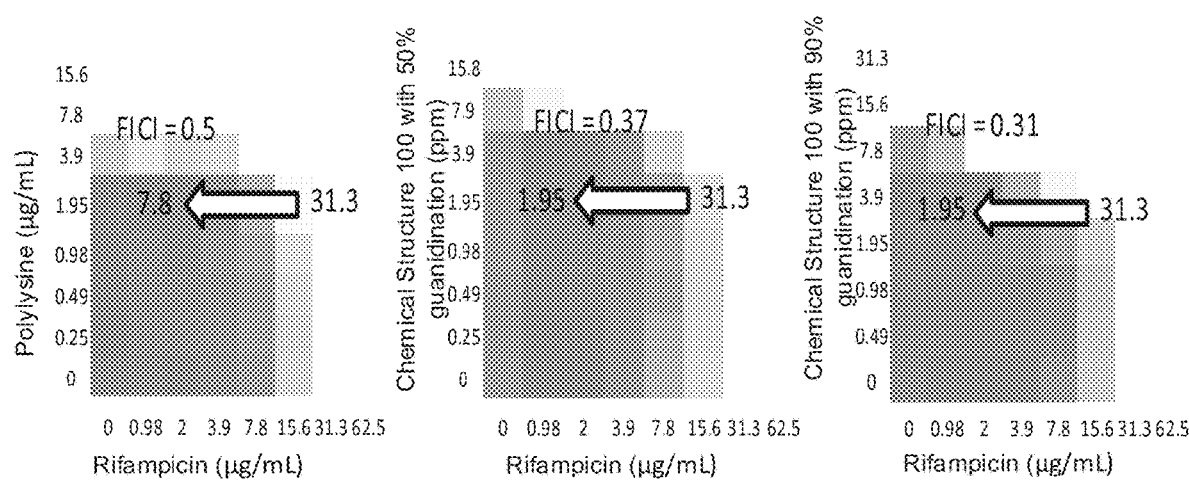
FIG. 4B illustrates a diagram of example, non-limiting graphs that can depict the efficacy of one or more combination therapies comprising one or more guanidinium functionalized polylysine polymers in combination with Rifampicin in accordance with one or more embodiments described herein.

FIGS. 4A-4B illustrates diagrams of example, non-limiting graphs that can depict the efficacy of one or more combination therapies comprising one or more guanidinium functionalized polymers in combination with one or more antibiotic in accordance with one or more embodiments described herein. Repetitive description of like elements employed in other embodiments described herein is omitted for sake of brevity. As shown in FIGS. 4A and/or 4B, exemplary combination therapies can comprise one or more polylysine polymers with various degrees of guanidinium functionalization along with Ceftiofur, Enrofloxacin, Chlortetracycline, and/or Rifampicin. For example, the combination therapies depicted in FIGS. 4A and/or 4B regard the treatment of K. pneumoniae.

Further, Table 1, presented below, can depict the antimicrobial activity of the guanidinium functionalized polylysine polymers and/or antibiotics individually with regards to K. pneumoniae. Guanidinium functionalized polylysine polymers have comparable MIC as compared to unmodified polylysine.

TABLE 1

| Chemical Compound | MIC (μg/mL) |
| --- | --- |
| Polylysine | 7.8 |
| Chemical Structure 100 (50% guanidination) | 15.6 |
| Chemical Structure 100 (90% guanidination) | 15.6 |
| Rifampicin | 31.3 |
| Ceftiofur | 4.0-8.0 |
| Enrofloxacin | 1.0 |
| Chlortetracycline | 15.6 |

As shown in FIGS. 4A and/or 4B (e.g., in comparison with Table 1), the combination of the one or more guanidinium functionalized polylysine polymers and the antibiotics has a synergistic effect. For example, a fractional inhibitory concentration index ("FICI") of: ≤0.5 is indicative of a synergistic effect; 0.5 to 1 is indicative of an additive effect; 1 to 4 is indicative of indifference to the combination; and/or >4 is indicative of an antagonistic effect. The synergistic effect achieved by the combination therapy increases with the degree of guanidinium functionalization of the polylysine polymers.

Figure 5:
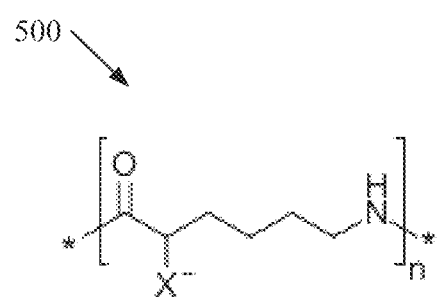
FIG. 5 illustrates a diagram of an example, non-limiting chemical structure that can characterize one or more anionic functionalized polylysine polymers in accordance with one or more embodiments described herein.

FIG. 5 illustrates a diagram of an example, non-limiting third chemical structure 500 that can characterize one or more anionic functionalized polylysine polymers in accordance with one or more embodiments described herein. Repetitive description of like elements employed in other embodiments described herein is omitted for sake of brevity. In various embodiments, the selectivity of antimicrobial and/or anticancer activity of the one or more guanidinium functionalized polylysine polymers can be significantly enhanced by the introduction of one or more anionic functionalized polylysine polymers (e.g., characterized by third chemical structure 500). As shown in FIG. 5, one or more anionic groups (e.g., represented by "X" in FIG. 5) can provide one or more negative charges to a polylysine structure. Example anionic groups (e.g., represented by "X" in FIG. 5) can include, but are not limited to: a sulfonate group, a carboxylate group, a phosphate group, a boronate group, a combination thereof, and/or the like.

For instance, the one or more guanidinium functionalized polylysine polymers (e.g., characterized by first chemical structure 100 and/or second chemical structure 102) can be combined with one or more anionic functionalized polylysine polymers (e.g., characterized by third chemical structure 500) to generate an electrostatic coacervate complex that is neutral and can shield toxicity of the one or more guanidinium functionalized polylysine polymers when the complex circulates throughout a body, thereby reducing the toxicity of the one or more guanidinium functionalized polylysine polymers to mammalian cells. In some embodiments, the coacervate complexes can be formed by administering the one or more guanidinium functionalized polylysine polymers in the presence of an anionic group.

These coacervate complexes can be well-defined nano-complexes that are highly modular with tunable particle size and neutral charge and remain stable under physiological conditions even in the presence of serum proteins. In some implementations, the coacervate complexes can be functionalized even further with biotin to further increase the uptake of the coacervate complex by the pathogen and/or cancer cells. In one or more additional embodiments, these coacervate complexes can be used for diagnostic purposes. With these embodiments, the one or more guanidinium functionalized polylysine polymers can be calibrated to target a specific pathogen or cancer cell type, and the one or more guanidinium functionalized polylysine polymers can be functionalized with a fluorescent dye that illuminates in response to reaction of the coacervate complex with the specific pathogen or cancer cell type.

Figure 6:
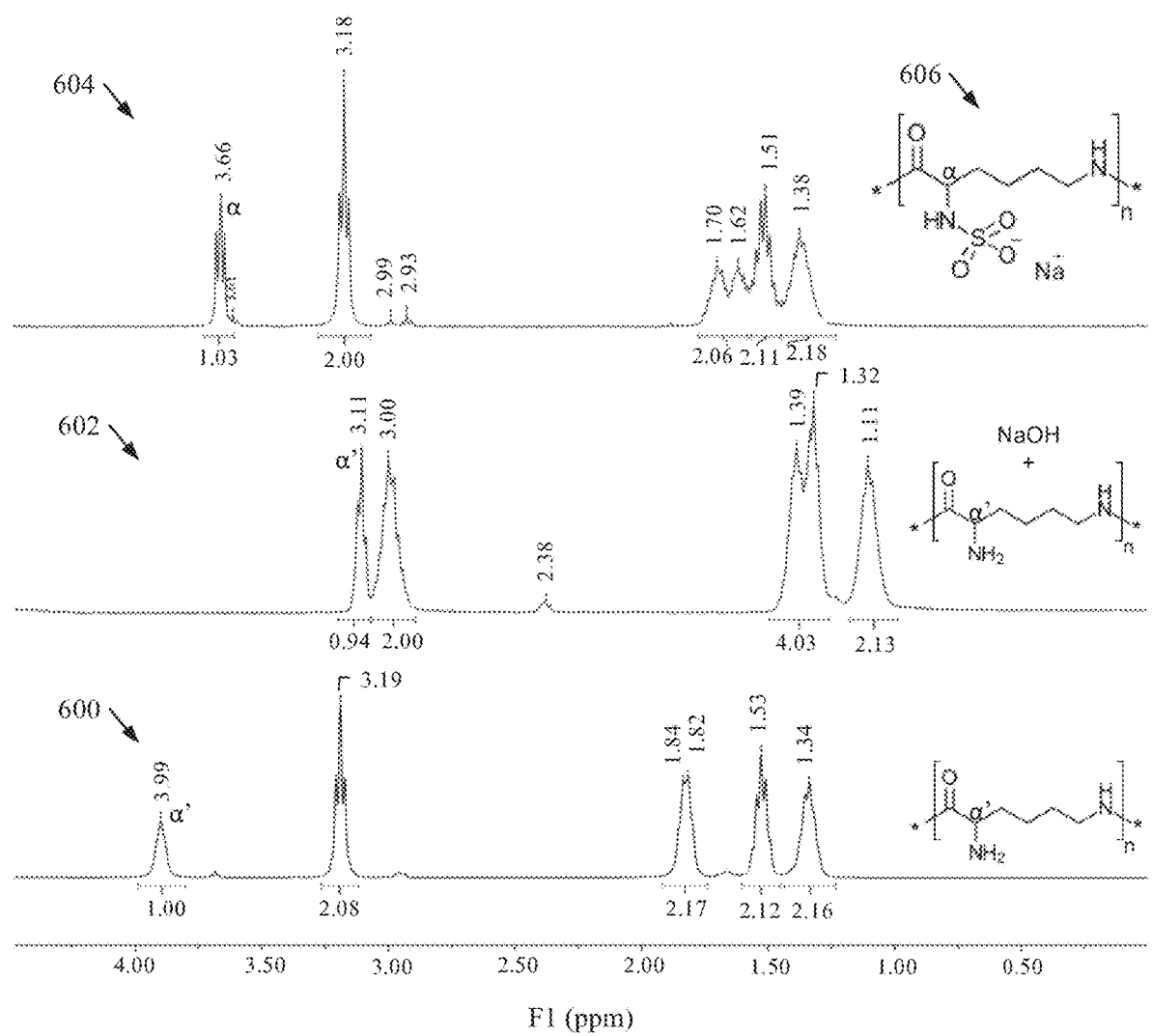
FIG. 6 illustrates a diagram of example, non-limiting graphs and corresponding nuclear magnetic resonance spectra that can depict various degrees of anionic functionalization of one or more polylysine polymers that can exhibit compatibility with one or more complex formulations in accordance with one or more embodiments described herein.

FIG. 6 illustrates a diagram of example, non-limiting NMR graphs that can demonstrate functionalization of the one or more anionic functionalized polylysine polymers in accordance with one or more embodiments described herein. Repetitive description of like elements employed in other embodiments described herein is omitted for sake of brevity.

The sixth NMR graph 600, shown in if FIG. 6, can correspond to a polylysine polymer. The seventh NMR graph 602, shown in FIG. 6, can correspond to a polylysine polymer in the presence of sodium hydroxide ("NaOH"). The eighth NMR graph 604, shown in FIG. 6, can correspond to a sulfonate functionalized polylysine polymer having about 100% functionalization with the one or more sulfonate groups. In various embodiments, the sulfonate functionalized polylysine polymer characterized in FIG. 6 can be an example anionic functionalized polylysine polymer, and/or can be characterized by fourth chemical structure 606, which can be in accordance with third chemical structure 500. As shown in FIG. 6, the amount of functionalization by the one or more anionic groups in an anionic functionalized polylysine polymer can also be monitored via NMR.

Figure 7:
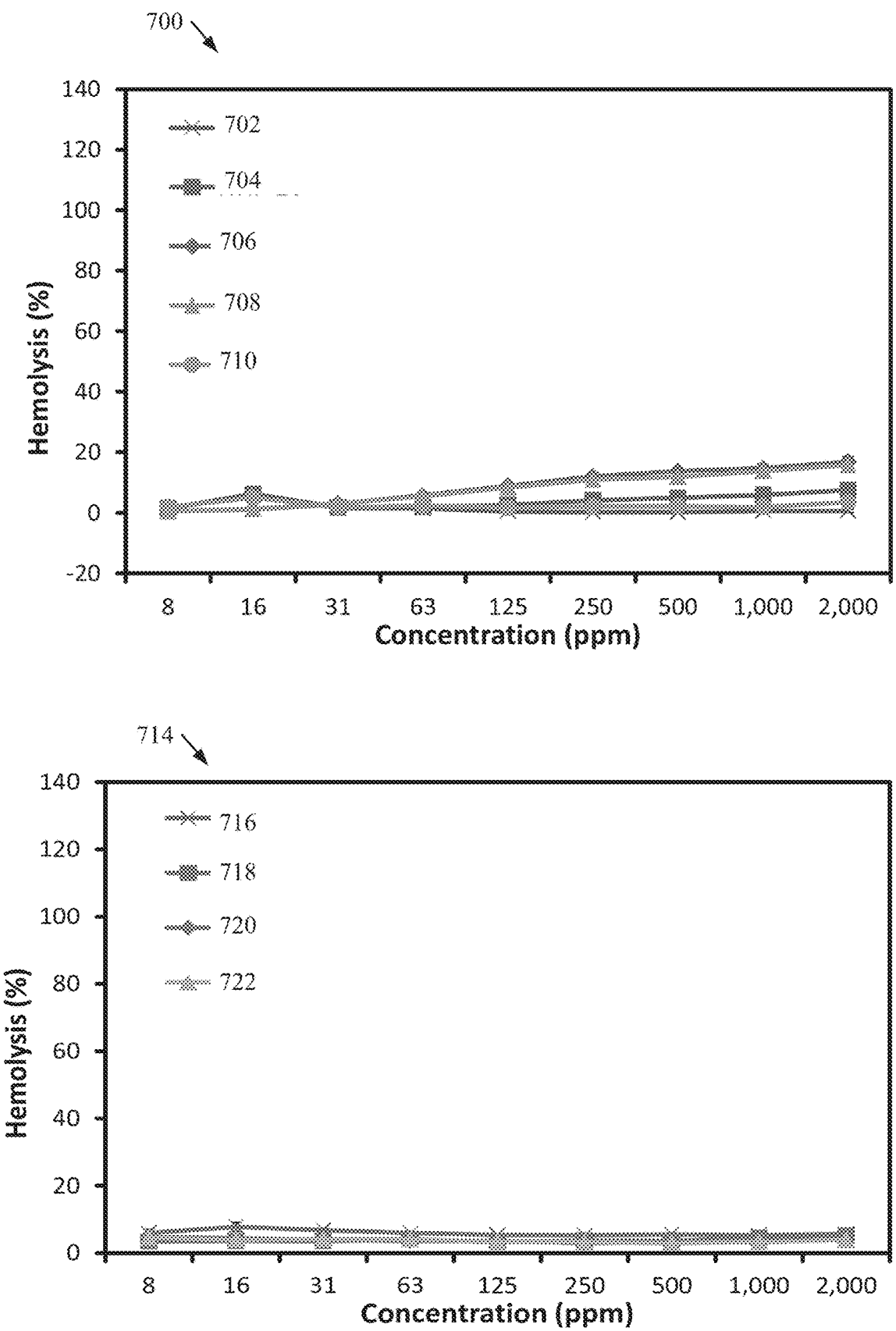
FIG. 7 illustrates a diagram of example, non-limiting graphs that can depict the hemolytic activity of one or more guanidinium-functionalized polylysine polymers in accordance with one or more embodiments described herein.

FIG. 7 illustrates a diagram of example, non-limiting graphs that can depict the hemolytic activity of the one or more guanidinium functionalized polylysine polymers and/or guanidinium functionalized polylysine polymer coacervate complexes in accordance with one or more embodiments described herein. Repetitive description of like elements employed in other embodiments described herein is omitted for sake of brevity.

Graph 700 regards the hemolytic activity of one or more guanidinium functionalized polylysine polymers characterized by the first chemical structure 100 and/or the second chemical structure 102. Line 702 represents the hemolytic activity of a sulfonate functionalized polylysine polymer (e.g., as depicted in FIG. 6) having about 100% sulfonation. Line 704 represents the hemolytic activity of a guanidinium functionalized polylysine polymer (e.g., as depicted in FIGS. 1 and/or 2) having about 50% guanidination. Line 706 represents the hemolytic activity of a guanidinium functionalized polylysine polymer (e.g., as depicted in FIGS. 1 and/or 2) having about 70% guanidination. Line 708 represents the hemolytic activity of a guanidinium functionalized polylysine polymer (e.g., as depicted in FIGS. 1 and/or 2) having about 90% guanidination. Line 710 can represent the hemolytic activity of a non-functionalized polylysine polymer.

Graph 714 regards the hemolytic activity of one or more guanidinium functionalized polylysine polymer coacervate complexes. The Line 716 represents the hemolytic activity of a guanidinium functionalized polylysine polymer coacervate complex comprising a guanidinium functionalized polylysine polymer (e.g., as depicted in FIGS. 1 and/or 2) having about 50% guanidination and a sulfonate functionalized polylysine polymer (e.g., as characterized by fourth chemical structure 606) having about 100% sulfonation. Line 718 represents the hemolytic activity of a guanidinium functionalized polylysine polymer coacervate complex comprising a guanidinium functionalized polylysine polymer (e.g., as depicted in FIGS. 1 and/or 2) having about 70% guanidination and a sulfonate functionalized polylysine polymer (e.g., as characterized by fourth chemical structure 606) having about 100% sulfonation. Line 720 represents the hemolytic activity of a guanidinium functionalized polylysine polymer coacervate complex comprising a guanidinium functionalized polylysine polymer (e.g., as depicted in FIGS. 1 and/or 2) having about 90% guanidination and a sulfonate functionalized polylysine polymer (e.g., as characterized by fourth chemical structure 606) having about 100% sulfonation. Line 722 represents the hemolytic activity of a guanidinium functionalized polylysine polymer coacervate complex comprising a guanidinium functionalized polylysine polymer (e.g., as depicted in FIGS. 1 and/or 2) having about 100% guanidination and a sulfonate functionalized polylysine polymer (e.g., as characterized by fourth chemical structure 606) having about 100% sulfonation. As depicted between graph 700 and/or graph 714, incorporating the one or more guanidinium functionalized polylysine polymers into one or more coacervate complexes with one or more anionic functionalized polylysine polymers can lower the hemolytic activity of the one or more guanidinium functionalized polylysine polymers.

Table 2, presented in FIG. 8A, further depicts the antimicrobial activity of the polymers and/or coacervate complexes depicted in graph 700 and/or graph 714. In combination, FIG. 7 and Table 2 exemplify that the one or more guanidinium functionalized polylysine polymers can have strong antimicrobial activity and/or that the coacervate complexes of the one or more guanidinium functionalized polylysine polymers can also exhibit antimicrobial activity while also exhibiting low levels of hemolytic activity.

FIGS. 8B-E illustrate diagrams of example, non-limiting graphs that can demonstrate the broad spectrum antimicrobial activity of the one or more guanidinium functionalized polylysine polymers (e.g., characterized by first chemical structure 100 and/or second chemical structure 102) in accordance with one or more embodiments described herein. Repetitive description of like elements employed in other embodiments described herein is omitted for sake of brevity.

FIG. 8B depicts the hemolytic activity of a guanidinium functionalized polylysine polymer characterized by chemical structure 100. Further, Table 3, presented below depicts the antimicrobial activity of a guanidinium functionalized polylysine polymer.

TABLE 3

| Chemical Compound | S. aureus (μg/mL) | E. coli (μg/mL) | P. aeruginosa (μg/mL) | C. albicans (μg/mL) | Hemolysis, $HC_{50}$ (μg/mL) |
|---|---|---|---|---|---|
| Chemical Structure 100 | 2 | 4 | 4 | 16 | >2000 |

FIG. 8C, depicts the antimicrobial activity of guanidinium functionalized polylysine polymer with regards to S. aureus bacteria, wherein an optical density of the bacteria was measured at a wavelength of 600 nanometers ("O.D. 600"). FIG. 8D, depicts the antimicrobial activity of guanidinium functionalized polylysine polymer with regards to E. coli bacteria. FIG. 8E, depicts the antimicrobial activity of guanidinium functionalized polylysine polymer with regards to P. aeruginosa bacteria.

Figure 9:
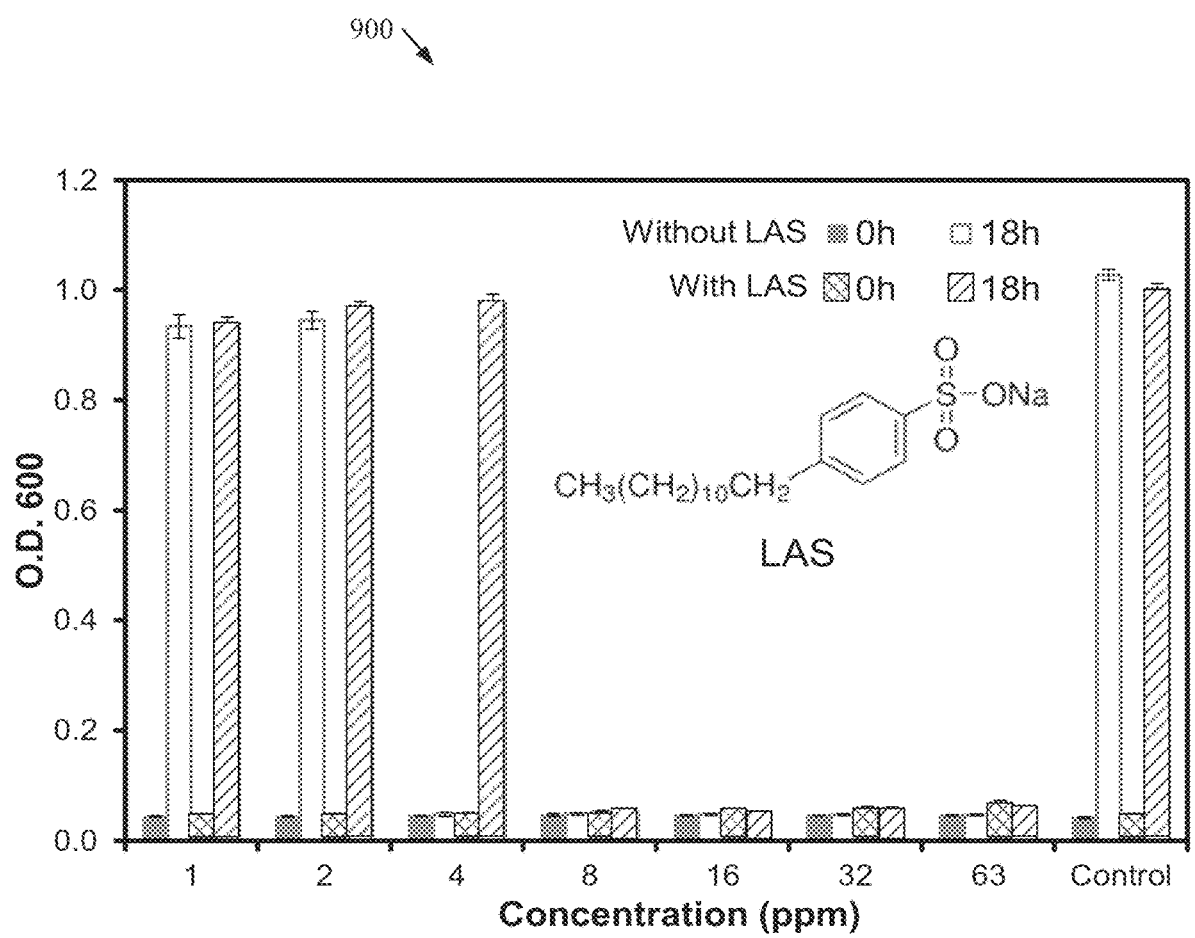
FIG. 9 illustrates a diagram of an example, non-limiting graph that can depict the antimicrobial activity of one or more guanidinium-functionalized polylysine polymers in accordance with one or more embodiments described herein.

FIG. 9 illustrates a diagram of an example, non-limiting graph 900 that can demonstrate the compatibility of the one or more guanidinium functionalized polylysine polymers with one or more complex formulations in accordance with one or more embodiments described herein. Repetitive description of like elements employed in other embodiments described herein is omitted for sake of brevity. For example, in various embodiments the one or more guanidinium functionalized polylysine polymers can be compatible with one or more complex chemical formulations. Example complex chemical formulations can include, but are not limited to: anionic surfactants, anionic polylysines, anionic polycarbonates, anionic polyesters, a combination thereof, and/or the like. For instance, FIG. 9 demonstrates the antimicrobial activity of the one or more guanidinium functionalized polylysine polymers in the presence of the exemplary anionic surfactant LAS (e.g., characterized by the chemical structure depicted in FIG. 9).

Figure 10:
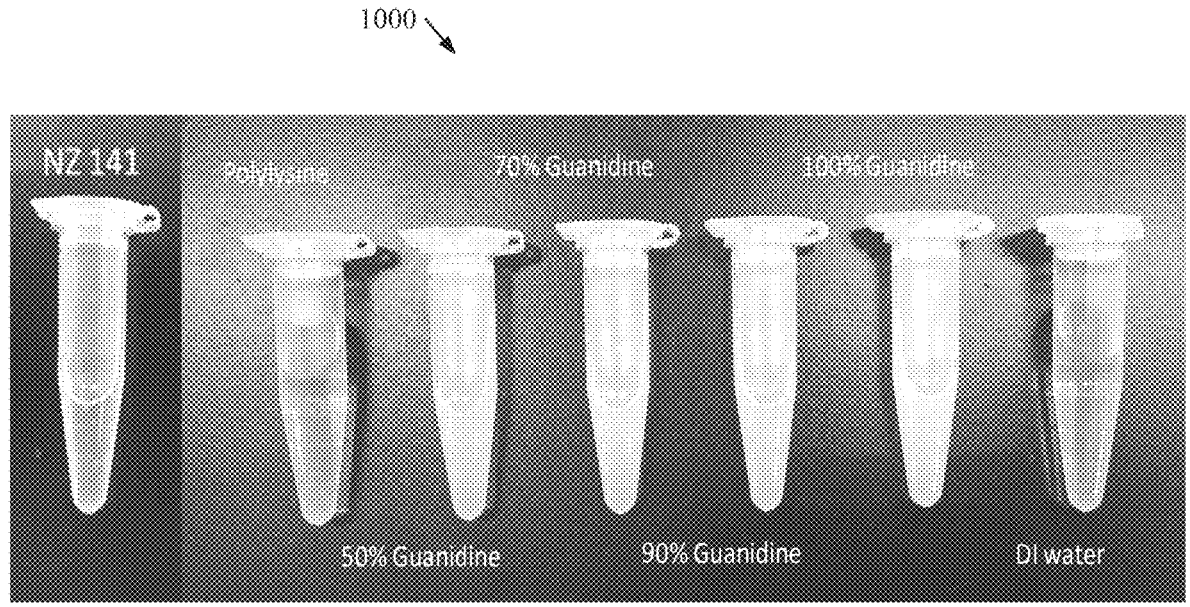
FIG. 10 illustrates a photo of example, non-limiting polylysine polymers to demonstrate compatibility with one or more surfactants in accordance with one or more embodiments described herein.

FIG. 10 illustrates a diagram of an example, non-limiting photo 1000 that can depict the amount of precipitation experienced by the one or more guanidinium functionalized polylysine polymers in water in accordance with one or more embodiments described herein. Repetitive description of like elements employed in other embodiments described herein is omitted for sake of brevity. As shown in FIG. 10, the amount of guanidination of the one or more guanidinium functionalized polylysine polymers can affect the precipitation properties of the polymers. For example, the one or more guanidinium functionalized polylysine polymers can exhibit greater precipitation as guanidination increases.

Figure 11:
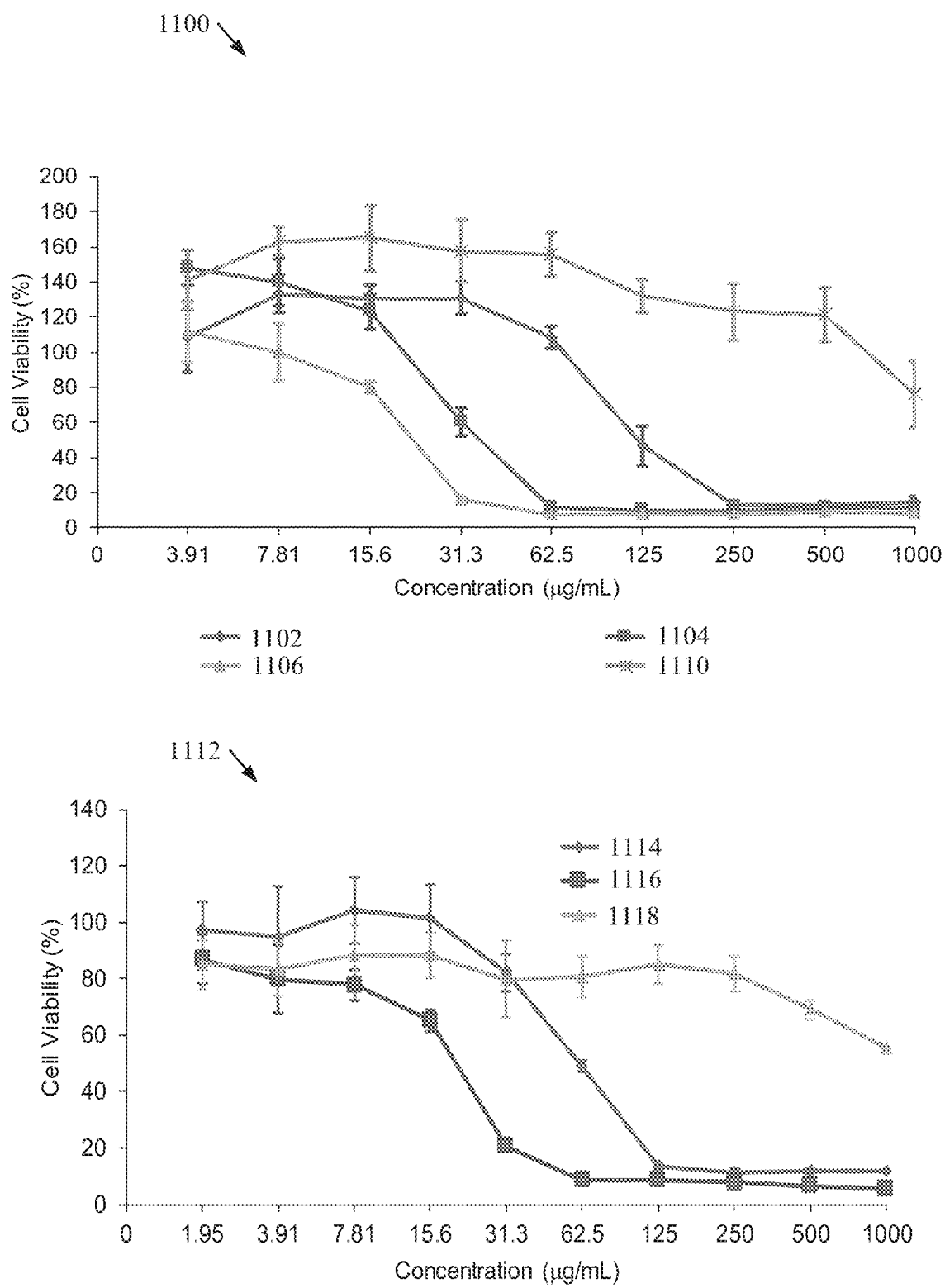
FIG. 11 illustrates a diagram of example, non-limiting graphs that can depict the anticancer activity of one or more guanidinium-functionalized polylysine polymers in accordance with one or more embodiments described herein.

FIG. 11 illustrates diagrams of example, non-limiting graphs that can depict the anticancer activity of the one or more guanidinium functionalized polylysine polymers in accordance with one or more embodiments described herein. Repetitive description of like elements employed in other embodiments described herein is omitted for sake of brevity.

Graph 1100 depicts the viability of BT-474 cells contacted with the one or more guanidinium functionalized polylysine polymers (e.g., characterized by first chemical structure 100 and/or second chemical structure 102) for 48 hours. Line 1102 represents the anticancer activity of a guanidinium functionalized polylysine polymer (e.g., as depicted in FIGS. 1 and/or 2) having about 50% guanidination. Line 1104 represents the anticancer activity of a guanidinium functionalized polylysine polymer (e.g., as depicted in FIGS. 1 and/or 2) having about 70% guanidination. Line 1106 represents the anticancer activity of a guanidinium functionalized polylysine polymer (e.g., as depicted in FIGS. 1 and/or 2) having about 90% guanidination. Line 1110 represents the anticancer activity of a non-functionalized polylysine polymer. Unmodified polylysine has $IC_{50}$ (inhibitory concentration of polymer leads to 50% cell viability) above 1000 μg/mL, while guanidinium-functionalized polylysine polymers have significantly lower $IC_{50}$ values, demonstrating greater cytotoxicity towards cancer cells. In addition, an increased guanidination degree results in greater anticancer activity.

Graph 1112 depicts the viability of Hep-G2 cells contacted with the one or more guanidinium functionalized polylysine polymers (e.g., characterized by first chemical structure 100 and/or second chemical structure 102) for 24 hours. Line 1114 represents the anticancer activity of a guanidinium functionalized polylysine polymer (e.g., as depicted in FIGS. 1 and/or 2) having about 50% guanidination. Line 1016 represents the anticancer activity of a guanidinium functionalized polylysine polymer (e.g., as depicted in FIGS. 1 and/or 2) having about 90% guanidination. Line 1118 represents the anticancer activity of a non-functionalized polylysine polymer. Guanidinium-functionalized polylysine polymers can have significantly lower $IC_{50}$ values than unmodified polylysine, demonstrating greater cytotoxicity towards cancer cells. In addition, an increased guanidination degree results in greater anticancer activity. For example, Table 4 depicts the $IC_{50}$ values of the guanidium-functionalized polylysine polymers described herein.

TABLE 4

| Polymer | $IC_{50}$ (μg/mL) |
|---|---|
| Polylysine | 508 |
| first chemical structure 100 (~50% guanidination) | 54.9 |
| first chemical structure 100 (~90% guanidination) | 21.3 |

Figure 12:
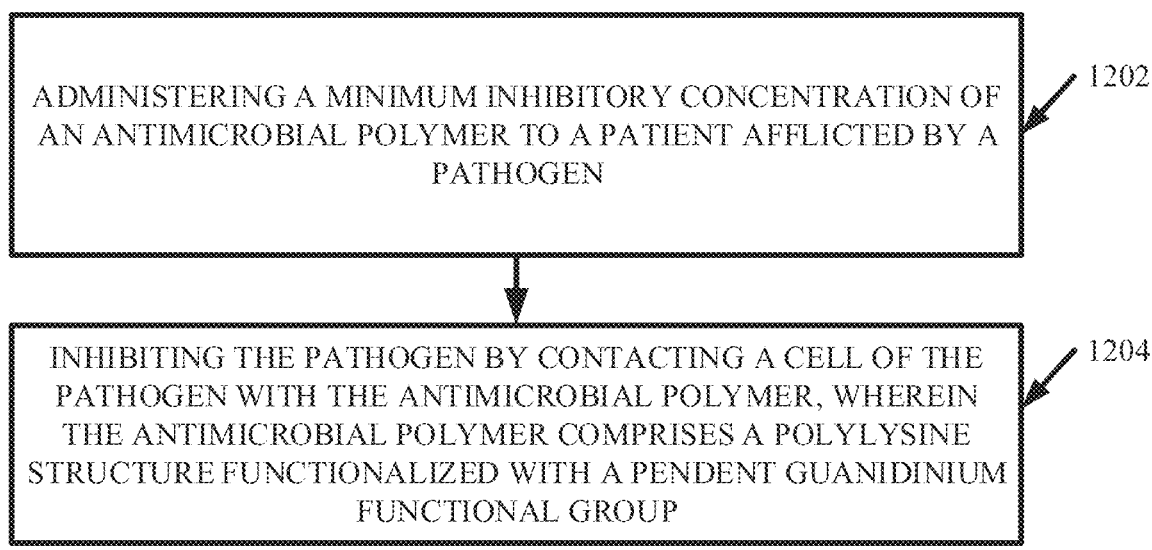
FIG. 12 illustrates a flow diagram of an example, non-limiting method that can inhibiting one or more pathogens using one or more guanidinium-functionalized polylysine polymers with antimicrobial and/or anticancer activity in accordance with one or more embodiments described herein.

FIG. 12 illustrates a flow diagram of an example, non-limiting method 1200 that can regarding inhibiting one or more pathogens via one or more guanidinium functionalized polylysine polymers in accordance with one or more embodiments described herein. Repetitive description of like elements employed in other embodiments described herein is omitted for sake of brevity.

At 1202, the method 1200 can comprise administering a MIC of one or more antimicrobial polymers to a patient afflicted by a pathogen. The pathogen can comprise, for example, a Gram-negative microbe, a Gram-positive microbe, a fungus, a yeast, a combination thereof, and/or the like.

At 1204, the method 1200 can comprise inhibiting the pathogen by contacting one or more cells of the pathogen with one or more antimicrobial polymers, wherein the one or more antimicrobial polymers can comprise one or more polylysine structures functionalized with one or more pendent guanidinium functional groups. For example, the one or more antimicrobial polymers can be characterized by the first chemical structure 100 and/or the second chemical structure 102. In one or more embodiments, the inhibiting at 1204 can be facilitated by the one or more antimicrobial polymers via a translocation mechanism that can comprise translocating the one or more antimicrobial polymers through a membrane of the cell and/or precipitating the one or more antimicrobial polymers within a cytosol of the cell. Thereby, the one or more antimicrobial polymers can interact with and/or precipitate one or more cytosolic members of the cell, such as one or more: proteins, enzymes, and/or genes.

In various embodiments, the one or more antimicrobial polymers can be comprised within a coacervate complex that further comprises one or more anionic polymers. The one or more anionic polymers can comprise one or more polylysine structures functionalized with one or more pendent anionic functional groups, such as, for example: a sulfonate group, a carboxylate group, and/or a phosphate group. For example, the one or more anionic polymers can be characterized by the third chemical structure 500.

In one or more embodiments, the one or more antimicrobial polymers can be comprised within a combination therapy with one or more antibacterial agents, wherein the antimicrobial polymer can enhance an antimicrobial activity of the antibacterial agent. For example, one or more cytosolic members targeted by the one or more antimicrobial polymers can be responsible for inhibiting one or more functions of the one or more antibacterial agents. Thereby, the antimicrobial activity of the one or more antibacterial agents can be enhanced by inhibiting (e.g., via boding and/or precipitation) the one or more cytosolic members by the one or more antimicrobial polymers.

Figure 13:
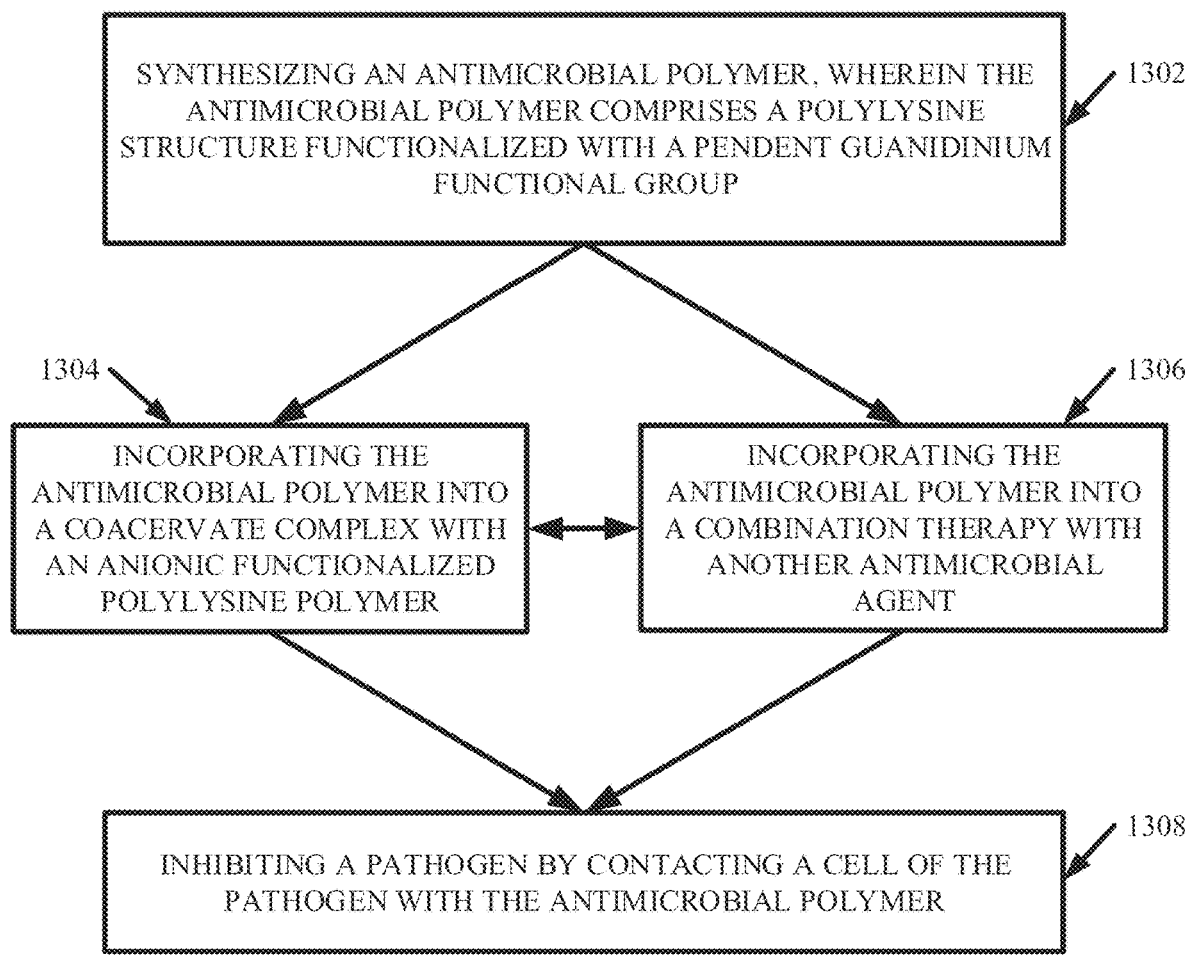
FIG. 13 illustrates a flow diagram of an example, non-limiting method that can inhibiting one or more pathogens using one or more guanidinium-functionalized polylysine polymers with antimicrobial and/or anticancer activity in accordance with one or more embodiments described herein.

FIG. 13 illustrates a flow diagram of an example, non-limiting method 1300 that can regarding inhibiting one or more pathogens via one or more guanidinium functionalized polylysine polymers in accordance with one or more embodiments described herein. Repetitive description of like elements employed in other embodiments described herein is omitted for sake of brevity.

At 1302, the method 1300 can comprise synthesizing one or more antimicrobial polymers, wherein the one or more antimicrobial polymers can comprise one or more polylysine structures functionalized with one or more pendent guanidinium functional groups. For example, the one or more antimicrobial polymers can be characterized by the first chemical structure 100 and/or the second chemical structure 102. In various embodiments, the synthesizing at 1302 can be performed in accordance with the one or more features of the first polymerization scheme 200 and/or the second polymerization scheme 202.

Additionally, in one or more embodiments the one or more antimicrobial polymers can be incorporated into one or more coacervate complexes and/or combination therapies. For example, at 1304 the method 1300 can comprise incorporating the one or more antimicrobial polymers into one or more coacervate complexes with one or more anionic functionalized polylysine polymers. For instance, the one or more anionic functionalized polylysine polymers can comprise one or more polylysine structures functionalized with one or more pendent anionic functional groups, such as, for example: a sulfonate group, a carboxylate group, and/or a phosphate group. For example, the one or more anionic functionalized polylysine polymers can be characterized by the third chemical structure 500. In various embodiments, a toxicity of the one or more antimicrobial polymers can be decreased by the incorporation at 1304.

In another example, at 1306 the method 1300 can comprise incorporating the one or more antimicrobial polymers into one or more combination therapies with one or more other antimicrobial agents (e.g., antibacterial agents). For instance, the one or more antimicrobial polymers can enhance an antimicrobial activity of the one or more other antimicrobial agents. For example, one or more cytosolic members targeted by the one or more antimicrobial polymers can be responsible for inhibiting one or more functions of the one or more antimicrobial agents. Thereby, the antimicrobial activity of the one or more antimicrobial agents (e.g., antibacterial agents) can be enhanced by inhibiting (e.g., via boding and/or precipitation) the one or more cytosolic members by the one or more antimicrobial polymers. In one or more embodiments, the one or more guanidinium functionalized polylysine polymers can be incorporated into both one or more coacervate complexes and/or combination therapies.

At 1308, the method 1300 can comprise inhibiting one or more pathogens by contacting one or more cells of the one or more pathogens with the one or more antimicrobial polymers. The pathogen can comprise, for example, a Gram-negative microbe, a Gram-positive microbe, a fungi, a yeast, a combination thereof, and/or the like. In one or more embodiments, the inhibiting at 1308 can be facilitated by the one or more antimicrobial polymers via a translocation mechanism that can comprise translocating the one or more antimicrobial polymers through a membrane of the cell and/or precipitating the one or more antimicrobial polymers within a cytosol of the cell. Thereby, the one or more antimicrobial polymers can interact with and/or precipitate one or more cytosolic members of the cell, such as one or more: proteins, enzymes, and/or genes. Wherein the one or more antimicrobial polymers are incorporated into one or more combination therapies, the one or more translocation mechanisms performed by the one or more antimicrobial polymers can enhance the activity of the one or more other antimicrobial agents.

Figure 14:
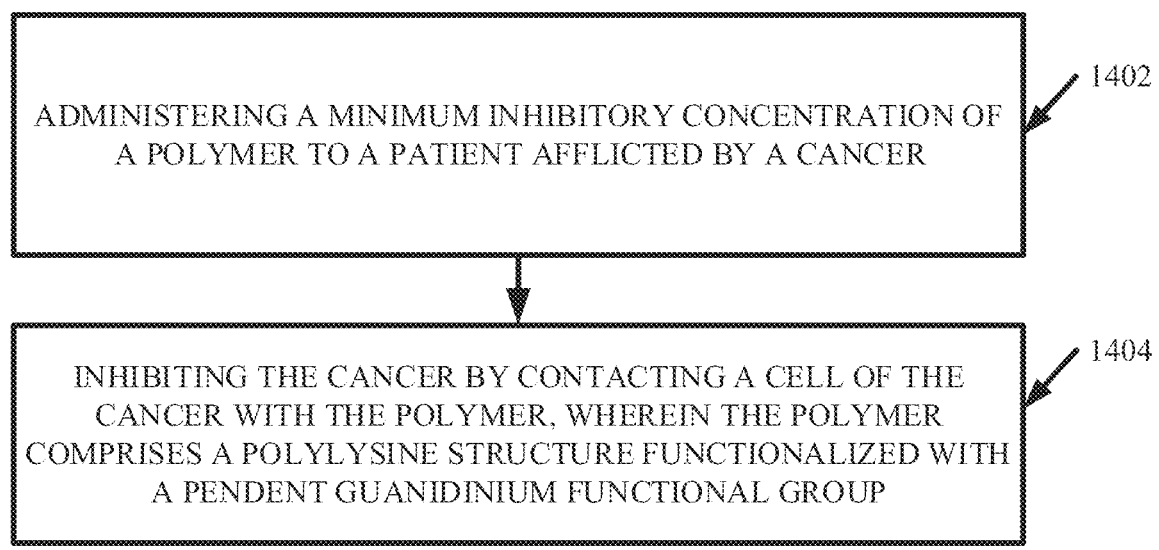
FIG. 14 illustrates a flow diagram of an example, non-limiting method that can inhibiting one or more cancers using one or more guanidinium-functionalized polylysine polymers with antimicrobial and/or anticancer activity in accordance with one or more embodiments described herein.

FIG. 14 illustrates a flow diagram of an example, non-limiting method 1400 that can regarding inhibiting one or more cancers via one or more guanidinium functionalized polylysine polymers in accordance with one or more embodiments described herein. Repetitive description of like elements employed in other embodiments described herein is omitted for sake of brevity.

At 1402, the method 1400 can comprise administering a MIC of one or more polymers to a patient afflicted by a cancer. The cancer can comprise, for example, BT-474 cells and/or Hep-G2 cells.

At 1404, the method 1400 can comprise inhibiting the cancer by contacting one or more cells of the cancer with one or more polymers, wherein the one or more polymers can comprise one or more polylysine structures functionalized with one or more pendent guanidinium functional groups. For example, the one or more polymers can be characterized by the first chemical structure 100 and/or the second chemical structure 102. In one or more embodiments, the inhibiting at 1404 can be facilitated by the one or more polymers via a translocation mechanism that can comprise translocating the one or more polymers through a membrane of the cell and/or precipitating the one or more polymers within a cytosol of the cell. Thereby, the one or more polymers can interact with and/or precipitate one or more cytosolic members of the cell, such as one or more: proteins, enzymes, and/or genes.

In various embodiments, the one or more polymers can be comprised within a coacervate complex that further comprises one or more anionic polymers. The one or more anionic polymers can comprise one or more polylysine structures functionalized with one or more pendent anionic functional groups, such as, for example: a sulfonate group, a carboxylate group, and/or a phosphate group. For example, the one or more anionic polymers can be characterized by the third chemical structure 500.

In one or more embodiments, the one or more polymers can be comprised within a combination therapy with one or more anticancer agents, wherein the polymer can enhance an anticancer activity of the anticancer agent. For example, one or more cytosolic members targeted by the one or more polymers can be responsible for inhibiting one or more functions of the one or more anticancer agents. Thereby, the anticancer activity of the one or more anticancer agents can be enhanced by inhibiting (e.g., via boding and/or precipitation) the one or more cytosolic members by the one or more polymers.

FIG. 15 illustrates a flow diagram of an example, non-limiting method 1500 that can regarding inhibiting one or more pathogens via one or more guanidinium functionalized polylysine polymers in accordance with one or more embodiments described herein. Repetitive description of like elements employed in other embodiments described herein is omitted for sake of brevity.

At 1502, the method 1500 can comprise synthesizing one or more polymers, wherein the one or more polymers can comprise one or more polylysine structures functionalized with one or more pendent guanidinium functional groups. For example, the one or more polymers can be characterized by the first chemical structure 100 and/or the second chemical structure 102. In various embodiments, the synthesizing at 1502 can be performed in accordance with the one or more features of the first polymerization scheme 200 and/or the second polymerization scheme 202.

Additionally, in one or more embodiments the one or more polymers can be incorporated into one or more coacervate complexes and/or combination therapies. For example, at 1504 the method 1500 can comprise incorporating the one or more polymers into one or more coacervate complexes with one or more anionic functionalized polylysine polymers. For instance, the one or more anionic functionalized polylysine polymers can comprise one or more polylysine structures functionalized with one or more pendent anionic functional groups, such as, for example: a sulfonate group, a carboxylate group, and/or a phosphate group. For example, the one or more anionic functionalized polylysine polymers can be characterized by the third chemical structure 500. In various embodiments, a toxicity of the one or more polymers can be decreased by the incorporation at 1404.

In another example, at 1506 the method 1500 can comprise incorporating the one or more polymers into one or more combination therapies with one or more anticancer agents. For instance, the one or more polymers can enhance an anticancer activity of the one or more anticancer agents. For example, one or more cytosolic members targeted by the one or more polymers can be responsible for inhibiting one or more functions of the one or more anticancer agents. Thereby, the anticancer activity of the one or more anticancer agents can be enhanced by inhibiting (e.g., via boding and/or precipitation) the one or more cytosolic members by the one or more polymers. In one or more embodiments, the one or more guanidinium functionalized polylysine polymers can be incorporated into both one or more coacervate complexes and/or combination therapies.

At 1508, the method 1500 can comprise inhibiting one or more cancers by contacting one or more cells of the one or more cancers with the one or more polymers. The cancer can comprise, for example, BT-474 cells and/or Hep-G2 cells. In one or more embodiments, the inhibiting at 1508 can be facilitated by the one or more polymers via a translocation mechanism that can comprise translocating the one or more polymers through a membrane of the cell and/or precipitating the one or more polymers within a cytosol of the cell. Thereby, the one or more polymers can interact with and/or precipitate one or more cytosolic members of the cell, such as one or more: proteins, enzymes, and/or genes. Wherein the one or more polymers are incorporated into one or more combination therapies, the one or more translocation mechanisms performed by the one or more polymers can enhance the activity of the one or more other anticancer agents.

As used throughout the present disclosure, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

It is, of course, not possible to describe every conceivable combination of components, products and/or methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A chemical composition, comprising:
a polymer comprising a molecular backbone covalently bonded to a pendent guanidinium functional group, wherein the molecular backbone comprises a polylysine structure, wherein the polymer exhibits antimicrobial activity against a pathogen, and wherein the polymer comprises 70% or greater functionalization with the pendent guanidium functional group.

2. The chemical composition of claim 1, wherein the pendent guanidinium functional group replaces a primary amine of the polylysine structure.

3. The chemical composition of claim 2, wherein the polylysine structure is selected from the group consisting of: ε-poly-L-lysine, and ε-poly-D-lysine.

4. The chemical composition of claim 1, wherein the pathogen is selected from the group consisting of: a Gram-negative microbe, a Gram-positive microbe, a fungus, and yeast.

5. The chemical composition of claim 1, further comprising:
a therapeutic agent, wherein the polymer enhances an activity of the therapeutic agent by interacting with a cytosolic member of a cell targeted by the activity, and wherein the therapeutic agent is selected from the group consisting of an antibacterial agent and an anticancer agent.

6. The chemical composition of claim 1, wherein the polymer is chemically compatible with an anionic surfactant.

7. The chemical composition of claim 1, further comprising:
a second polymer comprising a second molecular backbone covalently bonded to a pendent anionic functional group, wherein the second molecular backbone comprises another polylysine structure, and wherein the pendent anionic functional group is selected from the group consisting of: a sulfonate group, a carboxylate group, a boronate group, and a phosphate group.

8. The chemical composition of claim 1, wherein the polymer is characterized by a chemical formula:

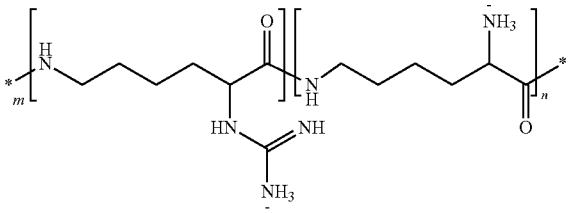

wherein "m" is a first number greater than or equal to 5 and less than or equal to 30; and
wherein "n" is a second number greater than or equal to 0 and less than or equal to 25.

9. The chemical composition of claim 1, wherein the polymer comprises 90% or greater functionalization with the pendent guanidium functional group.

10. The chemical composition of claim 1, wherein the antimicrobial activity comprises translocating through a membrane of a target pathogen cell and precipitating a biomacromolecule within a cytosol of the target pathogen cell.

11. A method, comprising:
inhibiting a pathogen by contacting a cell of the pathogen with an antimicrobial polymer, wherein the antimicrobial polymer comprises a polylysine structure functionalized with a pendent guanidinium functional group, and wherein the polymer exhibits antimicrobial activity against a pathogen, and wherein the polymer comprises 70% or greater functionalization with the pendent guanidium functional group.

12. The method of claim 11, wherein the inhibiting is facilitated by the antimicrobial polymer via a translocation mechanism that comprises translocating the antimicrobial polymer through a membrane of the cell and precipitating a biomacromolecule within a cytosol of the cell.

13. The method of claim 11, wherein the antimicrobial polymer is comprised within a coacervate complex that further comprises an anionic polymer, wherein the anionic polymer comprises another polylysine structure functionalized with a pendent anionic functional group, and wherein the pendent anionic functional group is selected from the group consisting of: a sulfonate group, a carboxylate group, a boronate group, and a phosphate group.

14. The method of claim 11, wherein the antimicrobial polymer is comprised within a combination therapy with an antimicrobial agent, wherein the antimicrobial polymer enhances an antimicrobial activity of the antimicrobial agent.

15. The method of claim 11, wherein the pathogen is selected from a group consisting of: a Gram-negative bacterium, a Gram-positive bacterium, a fungus, and yeast.

16. The method of claim 11, wherein the antimicrobial polymer is characterized by a chemical formula:

wherein "m" is a first number greater than or equal to 5 and less than or equal to 30; and
wherein "n" is a second number greater than or equal to 0 and less than or equal to 25.

17. An anticancer chemical composition, comprising:
a polymer comprising a molecular backbone covalently bonded to a pendent guanidinium functional group, wherein the molecular backbone comprises a polylysine structure, wherein the polymer exhibits anticancer activity, and wherein the polymer comprises 70% or greater functionalization with the pendent guanidium functional group.

18. The anticancer chemical composition of claim 17, wherein the polymer is characterized by a chemical formula:

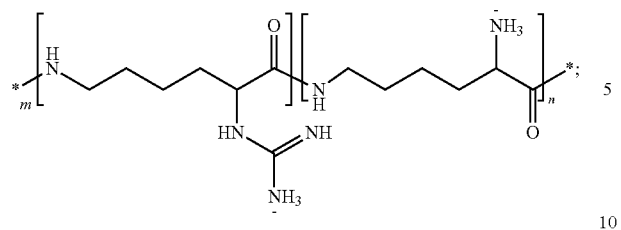

wherein "m" is a first number greater than or equal to 5 and less than or equal to 30; and wherein "n" is a second number greater than or equal to 0 and less than or equal to 25.

19. The anticancer chemical composition of claim 18, wherein the polymer comprises 90% or greater functionalization with the pendent guanidium functional group.

20. The anticancer chemical composition of claim 18, wherein the anticancer activity comprises translocating through a membrane of a target cancer cell and precipitating a biomacromolecule within a cytosol of the target cancer cell.

* * * * *